United States Patent [19]

Varco

[11] Patent Number: 4,749,507

[45] Date of Patent: Jun. 7, 1988

[54] PROCESS FOR REMOVING HAIR DYES FROM HAIR AND SKIN, AND PRODUCT FOR CARRYING OUT THE PROCESS

[75] Inventor: Joseph J. Varco, Fairfield, Conn.

[73] Assignee: Clairol, Incorporated, New York, N.Y.

[21] Appl. No.: 13,602

[22] Filed: Feb. 12, 1987

[51] Int. Cl.$^4$ .................................................. C11D 3/30
[52] U.S. Cl. ...................................... 252/91; 252/173; 252/548; 252/DIG. 5; 252/DIG. 13; 424/70; 514/846; 514/881; 514/944
[58] Field of Search ................ 252/91, 173, 544, 548, 252/DIG. 5, DIG. 13; 424/70; 514/846, 881, 944

[56] References Cited

U.S. PATENT DOCUMENTS

| | | | |
|---|---|---|---|
| 3,795,624 | 3/1974 | Feinstone | 252/91 |
| 3,939,260 | 2/1976 | Lafon | 252/91 |
| 4,290,904 | 9/1981 | Poper et al. | 252/132 |
| 4,321,167 | 3/1982 | Schmolka | 252/548 |
| 4,476,045 | 10/1984 | O'Lenick | 252/550 |
| 4,613,446 | 9/1986 | Magyar | 252/91 |

*Primary Examiner*—A. Lionel Clingman
*Assistant Examiner*—Hoa Van Le
*Attorney, Agent, or Firm*—Charles J. Zeller

[57] ABSTRACT

A towelette for removing hair dye from skin which comprises an abstract webbing partially or totally saturated with a solution of tetrahydroxypropryl ethylenediamine, the towelette being suitable for applying the solution to skin colored with hair dye, whereby the hair dye is removed from the skin.

2 Claims, No Drawings

PROCESS FOR REMOVING HAIR DYES FROM HAIR AND SKIN, AND PRODUCT FOR CARRYING OUT THE PROCESS

FIELD OF INVENTION

The present invention relates to the process for removing hair dyes from hair and skin and to products for carrying out the process. More particularly the present invention relates to the aforementioned process and a shampoo for removing hair dye from hair and a pretreated towelette for removing hair dye stains from skin.

BACKGROUND OF THE INVENTION

The only efficient way for removing undesirable hair dye from hair is by bleaching it, usually with strong oxidizers. This has the drawback of damaging the hair and irritating the scalp. Due to irritation problems, bleaches were never effective to allow removal of hair dye stains from skin.

DETAILED DESCRIPTION OF THE INVENTION

The present invention comprises a process for removing a hair dye from hair or skin by contacting the hair or skin with tetrahydroxypropyl ethylenediamine and then wiping or washing the diamine off the hair or skin. The invention further comprises a composition for removing the hair dye from hair wherein the composition is an amount of tetrahydroxypropyl ethylenediamine effective for removing hair dye from hair, dissolved in an aqueous shampoo base. The invention further comprises a towelette for removing hair dye stains from skin, which is an absorbent webbing partially or totally saturated with a solution of tetrahydroxypropyl ethylenediamine.

Tetrahydroxypropyl ethylenediamine is the CTFA name for N,N,N',N'-tetrakis(2-hydroxypropyl)ethylenediamine which has the following formula:

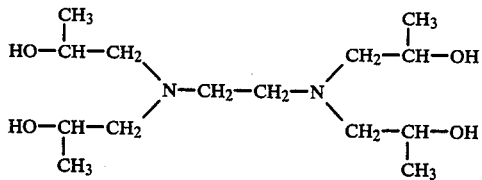

This compound is sold under the trade name Quadrol by BASF-Wyandotte Corporation. This material is sold for use as a cross linking agent and catalyst in producing polyurethane foams or as curing polyols for urethane coatings and as chemical intermediates, and is the subject matter U.S. Pat. No. 2,697,118. All of the foregoing information concerning tetrahydroxypropyl ethylenediamine, was obtained from the manufacturer's literature. Consequently, if there is any error in the chemical designation of this material by the manufacturer, the correct chemical entity referred to by the CTFA name is meant to be used throughout this application.

It was discovered that tetrahydroxypropyl ethylenediamine is, surprisingly, an excellent solvent for hair dyes, especially for certified dyes and direct dyes, and also on oxidative hair dyes if they are attempted to be removed reasonably soon after their application. In the case of oxidative hair dyes, as the amount of time between application and attempted removal increases, after a while the lighter dyes can be more effectively removed than the darker shades.

The term "shampoo base," as used throughout the specification and the claims, denotes any detergent composition suitable for use as a shampoo, as will be readily known by a person having average skill in the art.

In the application of a shampoo formula to hair, according to the present invention, the purpose of such use is generally for removing excess color that was applied to the hair, rather than try to remove the entire applied color.

The amount of tetrahydroxypropyl ethylenediamine useful for removing hair dye stains from skin or excess hair dye from the hair, is not critical. It has been found, however, that increasing the concentration of the material over 5% by weight does not appear considerably to improve the efficacy of dye removal.

Tetrahydroxypropyl ethylenediamine is very readily soluble in water, therefore, aqueous or aqueous/alcoholic solutions thereof can be readily used for impregnating towelettes in accordance with the present invention. The addition of an alcohol, such as ethanol, isopropanol, ethylene or diethylene glycol, hexylene glycol, butylene glycol, carbitol and the like sometimes amplify the effect, as well as contribute to faster drying.

Instead of pre-impregnated towelettes, one can also successfully employ tetrahydroxypropyl ethylenediamine-containing compositions in a gel or a cream base applied by means such as cotton or the like.

The following few examples are merely illustrative of the present invention:

EXAMPLE 1

The following alcohol-water solution is used for impregnating absorbent paper towelettes in accordance with the present invention. All percentages are by weight.

| | |
|---|---|
| tetrahydroxypropyl ethylenediamine | 0.1–10% |
| polyethylene glycol ether | 0.1–0.5% |
| fatty alcohols | |
| preservatives | 0.1–0.5% |
| perfumes | 0.2–0.8% |
| ethanol | 10.0–40.0% |
| water | to 100 |

The ethanol can be omitted if not required.

EXAMPLE 2

This example is a shampoo composition.

| | |
|---|---|
| cocobetaine | 5–8% |
| sodium lauroyl sarcosinate | 12.5–22.5% |
| lauramide DEA | 4–10% |
| tetrahydroxy propyl ethylenediamine | 0.1–10% |
| preservatives | 0.1–0.25% |
| antioxidants | 0.1–0.5% |
| perfumes | 0.2–0.5% |
| water | to 100 |

EXAMPLE 3

The following is a gel-base composition:

| | |
|---|---|
| carboxy vinyl polymer | 0.3–0.75% |
| triethanol amine | 0.3–0.75% |

| -continued | |
|---|---|
| tetrahydroxy propyl ethylenediamine | 0.1–10% |
| EDTA-4Na | 0.05–0.1% |
| preservatives | 0.1–0.25% |
| perfumes | 0.2–0.5% |
| water | to 100 |

We claim:

1. A towelette for removing hair dye from skin, which comprises an absorbent webbing partially or totally saturated with a solution containing from about 0.1 to about 10% by weight of tetrahydroxypropyl ethylenediamine, said towelette being suitable for applying said solution to skin colored with hair dye, whereby the hair dye is removed from the skin.

2. The towelette of claim 1, wherein said solution is an aqueous/alcohol solution.

* * * * *